United States Patent [19]

Schleufe et al.

[11] Patent Number: 5,791,340
[45] Date of Patent: Aug. 11, 1998

[54] RESUSCITATOR

[75] Inventors: Petra Schleufe; Hans Peter Reiffen, both of Hannover, Germany

[73] Assignee: Ambu International A/S, Glostrup, Denmark

[21] Appl. No.: 743,452

[22] Filed: Sep. 16, 1996

[30] Foreign Application Priority Data

Mar. 17, 1994 [DE] Germany .................. 44 09 076.5

[51] Int. Cl.$^6$ .................................................. A61M 16/00
[52] U.S. Cl. .................. 128/203.28; 128/203.11; 128/203.12; 128/200.18; 128/203.15
[58] Field of Search .................. 128/205.13, 204.18, 128/200.18, 200.22, 200.23, 203.12, 202.28, 205.15, 205.24, 205.17, 203.28, 203.15

[56] References Cited

U.S. PATENT DOCUMENTS 3,262,446  7/1966  Stoner ........................ 128/205.24
4,029,093  6/1977  Kohnke ....................... 128/203.28
4,374,521  2/1983  Nelson et al. ................ 128/205.13
4,938,210  7/1990  Shene ......................... 128/203.12

FOREIGN PATENT DOCUMENTS

3135276A1  9/1981  Germany .
2139099    5/1984  United Kingdom .

Primary Examiner—Vincent Millin
Assistant Examiner—V. Srivastava
Attorney, Agent, or Firm—Thomas R. Vigil

[57] ABSTRACT

The resuscitator is used for performing artificial resuscitation on patients and it comprises a bag which, at its one end is provided with a patient valve, and at its opposite end is provided with an inlet valve for drawing in fresh ambient air. Between the surroundings and the bag interior, a small flow-through opening is provided, through which the bag may be supplied with the contents of a dosage aerosol for administration by inhalation, of pharmaceutically active air cells. This allows for optimal use of the resuscitator as an inhalation spacer.

17 Claims, 4 Drawing Sheets

RESUSCITATOR

This is a continuation of international application PCT/DK 95/00122 with an international filing date of 17 Mar., 1995, now abandoned.

BACKGROUND OF THE INVENTION

1. Field of the Invention

The invention relates to a use of a device for carrying out artificial respiration on a patient. The invention further relates to a constructed to allow the supply of the contents of a container to a bag for administration to a patient and constructing a flow through opening between the container and bag so that such opening has sufficient resistance to outflow from the bag that the actual function of the resuscitator comprising the bag is not significantly influenced.

2. Description of the Prior Art

Devices of this kind are known as resuscitators. They are used in the medical field when a patient is incapable of breathing correctly or when the patient does not breathe at all, e.g. in case of unconsciousness. Thus, resuscitators do not only belong in hospitals, but in particular in the standard equipment of the emergency cases of emergency physicians and ambulance personnel. In particular in emergencies, the emergency physician often has reason to administer artificial respiration to the patient by means of the resuscitator.

A device of the kind described in the introductory part is known from DE 3135276 A1.

However, it has been found during the daily use that in many instances the artificial respiration with known resuscitators is insufficient for the patient. Thus, in emergencies in case of a frequently occuring obstruction (constriction of the respiratory tracts, e.g. bronchial constriction) a need arises to administer medication to the patient.

The state of the art provides two options for this, viz. administration by inhalation of a dosage aerosol whereby the patient inhales the aerosol, or intravenous administration by means of a catheter where the drug is introduced into the blood stream as an injectable solution.

For administration by inhalation dosage aerosols are known which comprise a small bottle or container provided with a jacket in the form of an attached member with a mouthpiece and made to enwrap the bottle. The attached member is operated manually by pressure whereby the contents of the container are released through the mouthpiece by means of a spraying nozzle. The user orientates the mouthpiece towards his opened mouth so as to allow the aerosol to be inhaled. Of course, these known dosage aerosols presuppose that the user himself is capable of operating the device. In case of emergencies when the patient is incapable of doing so, such dosage aerosols are not applicable.

With a view to administration by inhalation the so-called spacers are also known. It is characteristic of a spacer that it comprises a large-volume container and a mouthpiece at its one end and a dosage aerosol shoulder at its other end. Whereas the effectiveness of the dosage aerosol described above, designated a hand sprayer, is very limited, the spacer distinguishes itself by a substantially increased effect. The fact that the container contents of the dosage aerosol is initially sprayed into the large-volume container results in an increase of the interpulmonary deposition of the aerosol due to a volume increase and an improved distribution. The advantage arises because the aerosol reaches the patient's lung to the widest extent possible completely when inhaled.

Compared to the dosage aerosol in the form of the hand sprayer, only small amounts of the drug sticks to the mouth cavity of the patient when using the spacer and the major part reaches his lungs following inhalation.

Weighing against the advantages of the spacer are its size and poor handiness due to the large-volume container. While the known dosage aerosol in the form of a hand sprayer having dimensions largely corresponding to those of a pocket lighter is carried along without problems, the spacer has substantially larger dimensions. A length of approximately 15-20 cm and a diameter of up to 13 cm are common. Such dimensions do not allow the patient to permanently carry a spacer and therefore, the use of the spacer is also primarily constricted to stationary or domestic use.

The comparatively large volume requirements of the spacer also mean that there is not enough room in the emergency physician's emergency case therefor as the equally large-volume resuscitator also occupies much space. It is a further inconvenience that the state of the art provides different spacers since respective manufacturers offer their own spacers to match their own dosage aerosols. This means that not all spacers suit all dosage aerosols and thus, the emergency physician will have to have several different spacers in his suitcase to allow for the relevant dosage aerosol to be used.

Thus, for the reasons set forth above, the spacers have not found use outside a hospital and the only alternative available has been the solution of intravenous administration since the syringe needed therefor requires much less space in the physician's suitcase than several large-volume spacers.

Admittedly, there is always the basic option available in emergencies of administering pharmacologically active substances to the patient, although it should be considered that the intravenous administration is associated with serious disadvantages. Thus, there may be side effects affecting the circulation of blood and the heart performance. If worst comes to worst a heart failure cannot be ruled out.

SUMMARY OF THE INVENTION

The invention helps to remedy this and has the object of providing a use of a device to carry out artificial respiration on a patient wherein the device is already present in the confined space available in the emergency case of an emergency physician.

This use is given in claim 1. It allows the administration of aerosols to a patient outside a hospital directly at the accident site for the patient.

It is a further object of the invention to provide a device of the kind described in the introductory part of claim 2 which enables administration of aerosolised drugs to the resuscitator bag in a simple manner. This is obtained by the characteristic features given in the characterizing portion of claim 2.

The device according to the invention is distinguished by comprising a flow-through opening between the surroundings and the bag interior through which the contents of a dosage aerosol container may be supplied to the bag of a device of the kind described in the introductory part, viz. a resuscitator, for the administration of inhalants to patients, said resuscitator still being available for use to its original purpose, viz. the carrying out of artificial respiration without having to close the opening.

This measure has been found to provide a simple means to allow a resuscitator known per se to be used as a spacer.

For the first time it is possible for the emergency physician to provide the advantageous administration by inhalation of a dosage aerosol instead of the disadvantageous solution of intravenously administering drugs to the patient.

The performance of the resuscitator as a means for carrying out artificial respiration on patients by the presence of a flow-through opening for aerosols depends on the flow-through opening possessing such high degree of flow resistance against the outflow of air from the bag interior that substantially the entire amount of air displaced due to compression of the bag flows through the patient's valve to his lungs. This flow resistance may be obtained by dimensioning the flow-through opening with a small cross sectional area.

Since today the emergency case of every emergency physician already contains a resuscitator this result may be obtained without making further demands to space in the emergency suitcase which, from a space point of view, is already strictly confined. The basic idea underlying the invention is thus, when need arises, to be able to make use of the bag of a resuscitator already present as the required large-volume container for a spacer. Thereby it is crucial that the relatively small flow-through opening due to the measures according to the invention does not influence the causal performance of the resuscitator. Thus, despite the said flow-through opening, the device according to the invention lends itself to the intended use as a resuscitator wherein the invention further advantageously allows for the further option of being able to administer aerosols to the patient when needed by inhalation by means of the resuscitator whereby the resuscitator serves as a spacer.

Since dosage aerosols are already present in the suitcase of the emergency physician, the invention does not give rise to a need for more space. As known in connection with the spacer, the container contents are supplied through the spraying valve of the dosage aerosol into the resuscitator bag through the flow-through opening according to the invention, said aerosol container containing the corresponding fluid and propellant whereby the volume increase and nebulization provided by the resuscitator allows for the same advantageous effect as the spacer and whereby the desired administration of aerosolised inhalants to the patient is allowed. Thus, the intravenous administration of drugs carried out directly on the accident site which is very risky is avoided and replaced by the inhalation therapy.

In this connection, it applies to the dosage aerosol that only the plain container itself is required so that the otherwise usual attached member with its mouthpiece and the jacket designed as a wrapping, respectively, may be omitted. Thus, it is sufficient to introduce the spraying nozzle of the dosage aerosol container into the entrance region of the flow-through opening according to the invention and thus to operate the spraying nozzle by pressure or by depression so that the container contents may be sprayed into the resuscitator bag.

According to one embodiment of the resuscitator the flow-through opening is provided in a constructive element mounted separately on the bag. This constructive element is advantageously made with an angular shape so as to allow the establishment thereon of an abutment by pressure activation of the spraying valve of the dosage aerosol. In this connection, an angle of approximately 90° is convenient.

The diameter of the tubular spraying nozzles of the known dosage aerosols is comparatively small thereby allowing realisation of a small flow-through opening. This is of significance as it is thereby ensured that the actual function of the resuscitation of performing artificial respiration on a patient is not affected due to the small flow-through opening. Thus, despite its flow-through opening, the device according to the invention may also still be used as a resuscitator. At the side facing away from the bag of the resuscitator, the flow-through opening is advantageously provided with a cone-like enlargement. However, a step-shaped design of this area is also an option.

This measure allows the invention to use several dosage aerosols with spraying nozzles of different diameters. Thus, in this embodiment the invention does not depend on the kind of dosage aerosol available to the physician at the site of accident. Due to the conelike or step-shaped enlargement of the flow-through opening, different kinds of dosage aerosols may be used where, in each instance, it is ensured that operation of the plain dosage aerosol container allows the spraying nozzle to obtain the required abutment and that the container contents may be sprayed into the bag volume.

According to one embodiment of the invention the inlet valve is provided with a bore wherein an adapter is disposed wherein the flow-through opening is arranged.

Tests have shown that it is sufficient to provide a flow-through opening with an internal diameter of about 0.5–1 mm. This small diameter ensures that the actual intended function of the resuscitator is not significantly affected by the presence of the small flow-through opening.

Further advantageous embodiments of the invention are described in the subclaims.

BRIEF DESCRIPTION OF THE DRAWINGS

Further embodiments of the invention will now be described in further detail with reference to the accompanying drawings, wherein.

DESCRIPTION OF THE PREFERRED EMBODIMENT(S)

Figure 1:
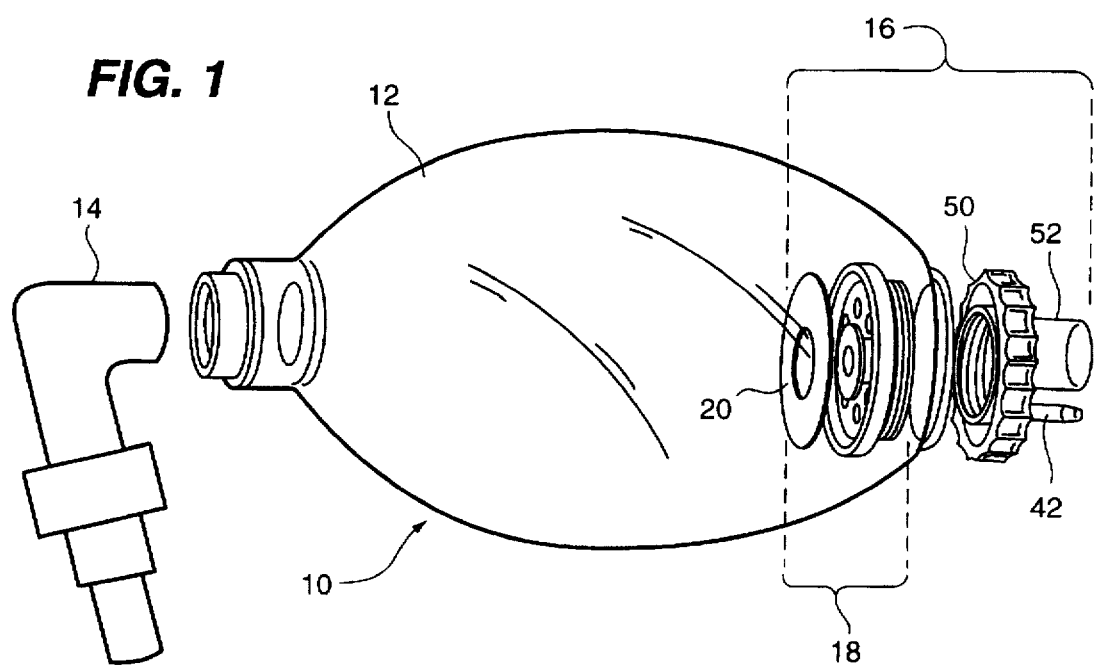
FIG. 1 is a known device in the form of a resuscitator.

For improved understanding of the invention, FIG. 1 of the drawings firstly illustrates a known device 10 in the form of a resuscitator and provided with a resuscitator bag 12 made up of a transparent silicon bag. On the side of the device 10 facing a patient, a valve 14 is provided and on the opposite side an inlet valve is arranged which as a unit is designated with the reference numeral 16. The valve 14 as well as the inlet valve 16 are transparent and consist of polysulphon.

Correct air flow through the bag 12 is ensured in a manner known per se by a double-lipped disc valve present in the valve 14 and not shown in detail herein.

The inlet valve 16 is made up of a single disc valve and consists in a known manner of a disc valve portion 18 present in the interior of the bag 12 and provided with a rubber disc 20 and an opposite annular member 50 provided outside the bag 12.

For the sake of clarity, the disc valve portion 18 and the annular portion 50 are shown separately in the drawings. In use, the two portions form a unit when screwed together whereby the open right end of the bag 12 is located between the disc valve portion 18 and the annular member 50.

For the air flow of the device 10 it is of no consequence whether it is effected by compression of the bag 12 or by suction at the patient's end, e.g. at the valve 14. Thereby it is possible to perform artificial respiration assisted as well as controlled.

On the annular member 50 yet a nipple 42 is present as well as a larger connector 52. Through this connector 52 communication may be provided in a manner known per se with an oxygen reservoir not shown in further detail in the drawings, whereas the small nipple further allows for the supply of oxygen to the bag 12.

Figure 2:
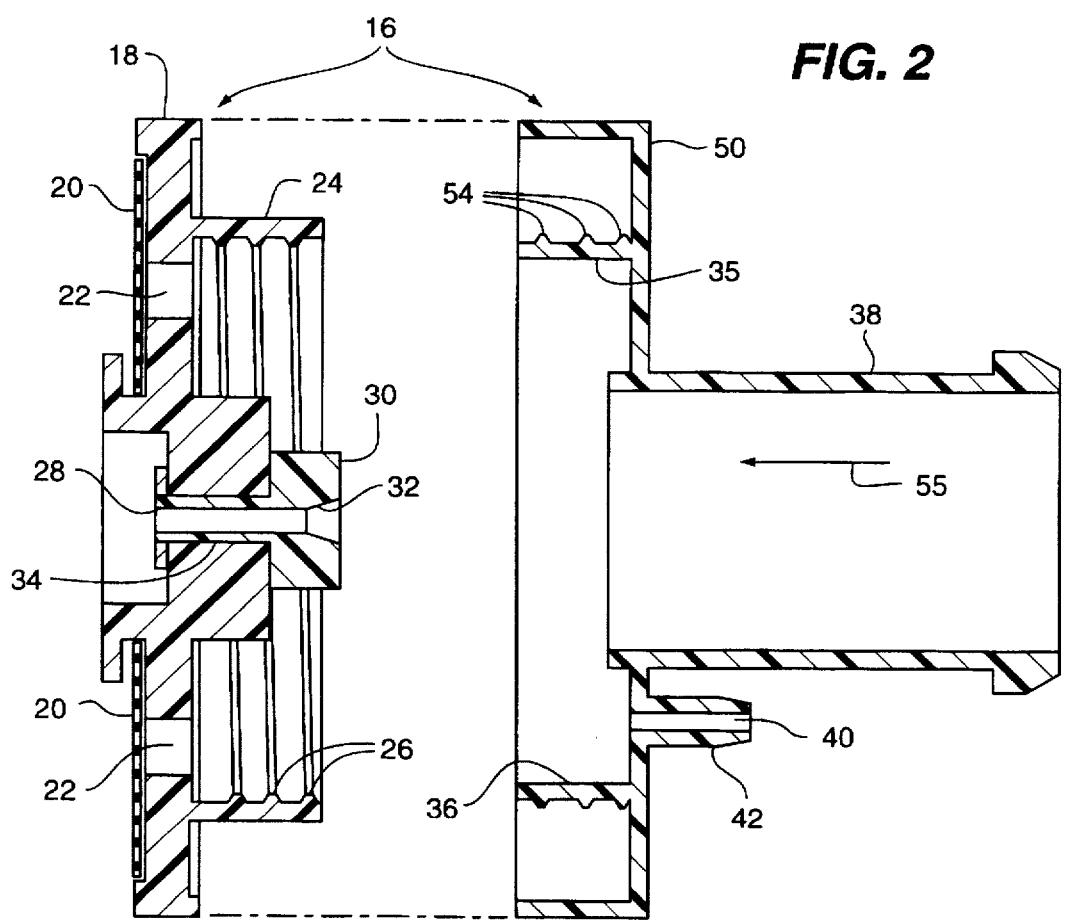
FIG. 2 is a sectional view of an inlet valve which is a part of a device according to the invention.

FIG. 2 is a sectional view of the inlet valve used with a device according to one embodiment of the invention and provided with a small flow-through opening 28 which is located centrally in the disc valve portion thereof. The diameter of the flow-through opening may be within about 1–2 mm and in any case it is so small that the presence of the flow-through opening does not significantly influence the actual intended and known function of the resuscitator 10.

Moreover, the sectional view according to FIG. 2 clarifies the fact that in addition to the rubber disc 20 the disc valve portion possesses several air openings 22 to enable the desired flow of air into the bag 12. On the side facing the annular member 50, the disc valve portion further has a first threaded ring 24 provided with an internal thread 26. To match this, the annular member 50 is provided with a second threaded ring 36 and an external thread 54 so as to allow the disc valve portion and the annular member 50 to be screwed together to form a unit.

Figure 4:
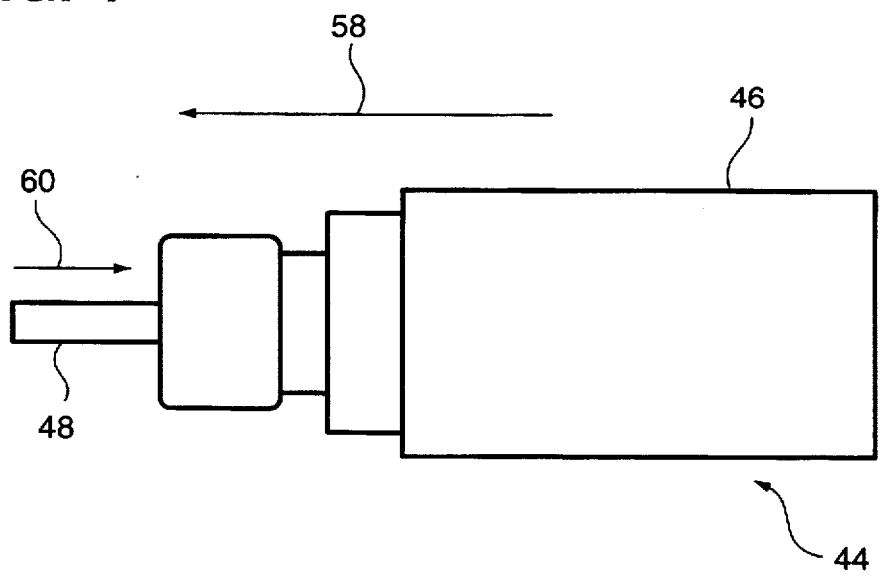
FIG. 4 is a dosage aerosol for use in connection with the device according to the invention.

Moreover the annular member 50 is shown with a guide socket 30 which serves partly as a handling aid by grip with the hand and partly as a guide to the container 46 of the dosage aerosol 44 which may be introduced into its opening as shown in FIG. 4.

Finally, the annular member 50 possesses a nipple 42 as mentioned in connection with FIG. 1 and provided with a flow-through bore 40 for use in case of additional oxygen supply.

The measure which is crucial to the invention consists in providing a flow-through opening 28 through which the contents of the container 46 of the dosage aerosol 44 may be supplied to the bag 12 for administration of the aerosol to a patient by inhalation. Hereby the device 10 is allowed to serve not only as a resuscitator but also surprisingly and in a manner unknown so far as a spacer.

It results from this that for the first time it is possible for the emergency physician to perform inhalation therapy directly at a site of accident, a resuscitator being standard equipment in the suitcase of an emergency physician, while, for reasons of space, it was not possible previously to bring along a spacer, which is considerably space consuming, in addition to a resuscitator.

Figure 3:
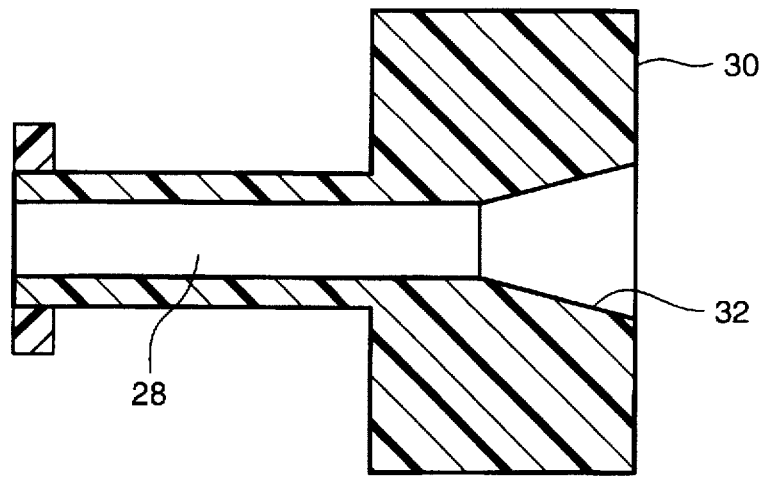
FIG. 3 is a detailed view of an adapter with a flow-through opening according to FIG. 2.

In the embodiment shown in FIG. 2 the disc valve portion 18 is provided with a central bore 34 wherein an adapter 30 is arranged. This adapter 30 possesses the actual flow-through opening 28 which on the side facing the annular member 50 is provided with a conically extending enlargement 32. The adapter 30 with the flow-through opening 28 and the conical enlargement 32 are shown enlarged in FIG. 3.

FIG. 4 shows a plain dosage aerosol 44 without the wrapping and jacket, respectively, usual to the known dosage aerosols in the form of hand sprayers, which are made redundant by the invention and thus dispensable. The dosage aerosol 44 has in a manner known per se a spraying valve 48 which, when operated, sprays the contents of the container 46 in the direction of the arrow 60.

According to the idea underlying the invention the dosage aerosol 44, cf. FIG. 4, according to one embodiment of the invention is introduced into the guide socket 38 (cf. FIG. 2) in the direction of the arrow 58 until the nipple of the spraying valve is in abutment on the conical enlargement 32 of the flow-through opening 28. Thus, the enlargement 32 helps to ensure that different types of dosage aerosols 44 may be used and even independently of the diameter of the respective spraying valve 48.

When the dosage aerosol is subsequently moved further in the direction of the arrows, 56 and 58 respectively, the spraying valve is released and activated. The suspension present in the propellant in the container 46 is now sprayed through the flow-through opening 28 into the bag 12 which then in a manner known per se takes over the function of the spacer. Finally, the patient is permitted to inhale the contents of the bag or supplementary artificial respiration is administered to him. Following the administration of artificial respiration, the dosage aerosol 44 may be left on site; it does not prevent replenishing of the bag 12.

The bag 12 being transparent allows the operator in charge to visually observe the aerosol thrust in the bag 12. Any contaminants are thus swiftly and safely left out. Following a number of dosage aerosol administrations, the bag should be cleaned with hot water. Since the bag 12 is always cleaned and disinfected following normal use as a resuscitator this does not in practice constitute additional requirements. In case of disposable resuscitators this is, of course, not necessary.

Figure 5:
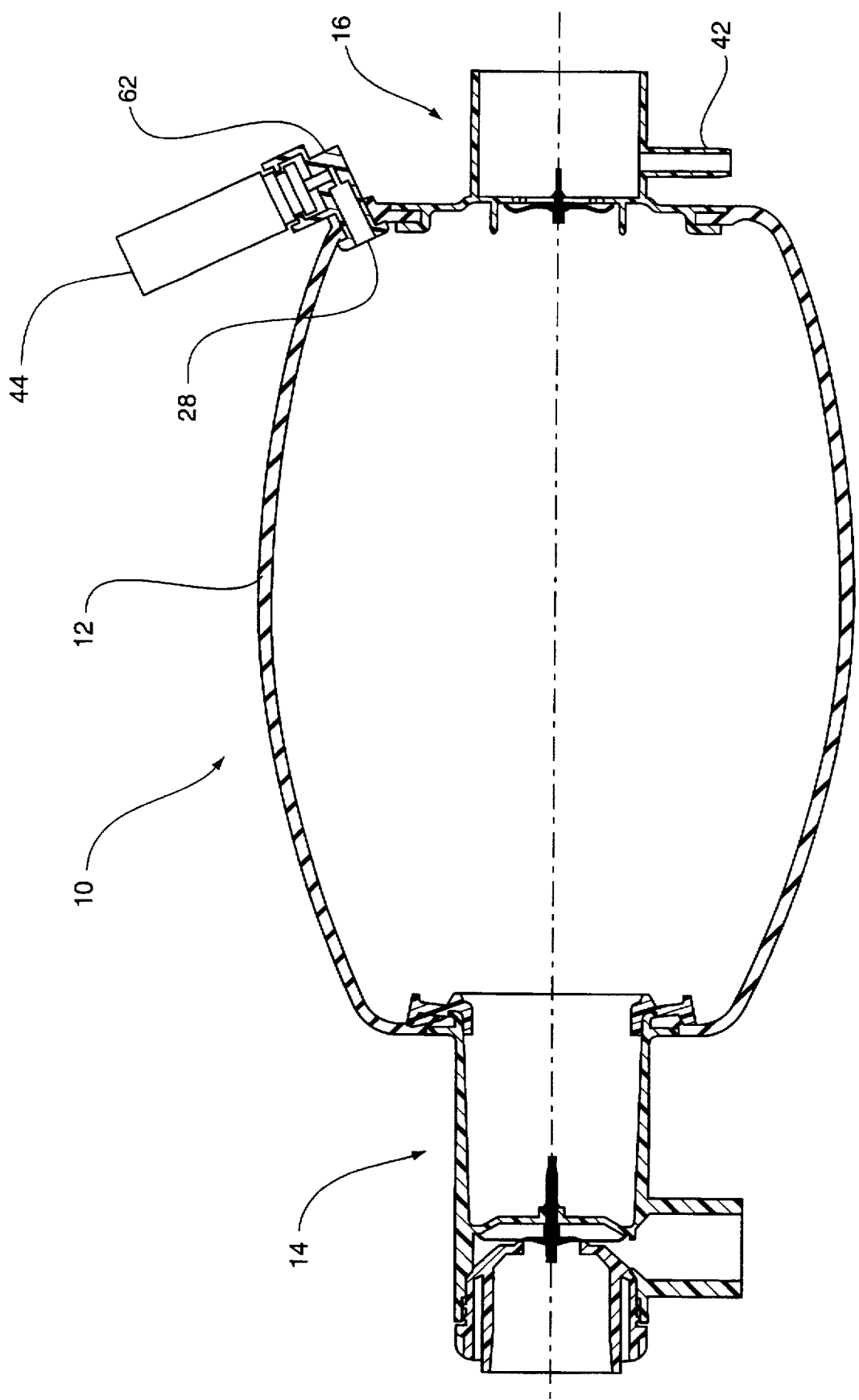
FIG. 5 is a sectional view of a second embodiment of the resuscitator according to the invention where the flow-through opening is provided in an angular boss mounted on the bag.

FIG. 5 illustrates members having the same function as the members shown in FIG. 1 and designated with the same reference numerals. The embodiment of the members shown in the two constructions differ from each other which, however, does not influence the functioning of the invention.

From FIG. 5 another embodiment of a resuscitator according to the invention will appear. Like the embodiment shown in FIG. 1, this resuscitator comprises a bag, an inlet valve and a patient valve. Adjacently the inlet valve, an angle socket is mounted on the bag. This socket contains the flow-through opening for the aerosol. Due to the angular shape it is possible to provide an abutment at the exertion of a pressure on the spraying nozzle of the container towards the portions of the surrounding wall material intended therefor.

Figure 6:
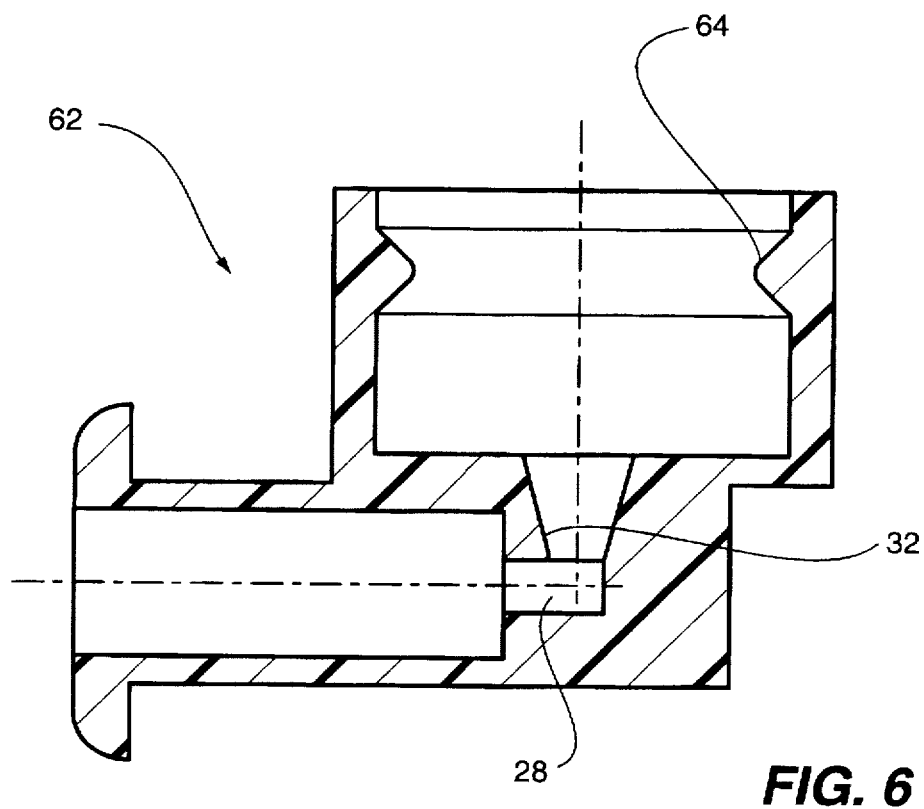
FIG. 6 is an enlarged sectional view of an embodiment of an angular boss.
Figure 7:
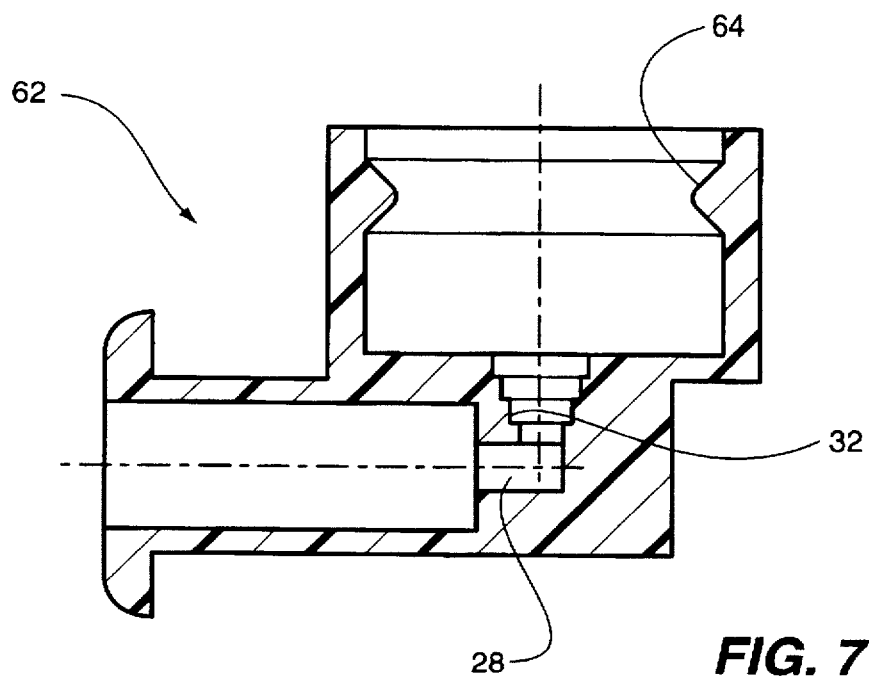
FIG. 7 is an enlarged sectional view of a second embodiment of an angular boss.

FIGS. 6 and 7 are enlarged views of two different embodiments of angle sockets for mounting on the bag of a resuscitator. As will appear the form of material in FIG. 6 is conically tapering in the direction towards the bag. As was the case with the adapter described in connection with FIG. 3, this allows the use of spraying nozzles with different diameters in connection with the resuscitator according to the invention. In FIG. 7 the wall material is provided with a step-shape. This also permits use of containers comprising spraying nozzles having different diameters.

It will appear from FIGS. 6 and 7 that the socket is provided with an annular bead 64 in the region to engage with the aerosol container 46. This bead 64 serves to releasably secure the container 46, as the bead 64 co-operates with a recess in the container. Hereby it is ensured that when carrying out artificial respiration, the container wil remain in its ready-for-use state. Subsequent supplementary administration of drugs may therefore be carried out with a minimum of handling.

We claim:

1. Resuscitator comprising a bag defining a boundary between a bag interior and a bag surrounding and being provided with means for self expansion after manual compression, a patient valve connected to the bag and providing a flow connection between the bag interior and the bag surrounding for providing a bag content to a patient upon compression of the bag, an inlet valve connected to the bag and providing a flow connection between the bag interior and the bag surrounding for drawing in fresh ambient air into the bag interior upon self expansion of the bag, and a flow-through channel provided with an inlet facing the bag surrounding and an outlet facing the bag interior, the flow-through channel having a minimal dimension to allow the supply of the contents of a container of a dosage aerosol to the bag for the administration to a patient by inhalation of its now aerosolized contents, and the flow-through channel having a maximal dimension providing so much flow resistance to outflow from the bag that the actual function of the resuscitator is not significantly influenced upon compression of the bag.

2. Resuscitator according to claim 1, wherein a separate constructive element is mounted on the bag and wherein the flow-through channel is provided in this constructive element.

3. Resuscitator according to claim 2, wherein the constructive element is angular in shape.

4. Resuscitator according to claim 1, wherein the flow-through channel is provided in the inlet valve.

5. Resuscitator according to claim 1, wherein the inlet valve is provided with a bore wherein an adapter for the flow-through channel is provided.

6. Resuscitator according to claim 1, wherein at its inlet, the flow-through channel is so constructed that a spraying valve of a dosage aerosol may be received in the opening and find abutment herein on the surrounding material.

7. Resuscitator according to claim 6, wherein the flow-through channel is designed with an outwardly oriented tapering for receiving the spraying valve.

8. Resuscitator according to claim 7, wherein the tapering extends conically.

9. Resuscitator according to claim 7, wherein the tapering extends stepwise.

10. Resuscitator according to claim 1, wherein the flow-through channel has a maximum diameter of 4 mm on the most narrow site.

11. Resuscitator according to claim 1, wherein means are provided about the flow-through opening to at least partially receive the container of the dosage aerosol provided with a spraying valve.

12. Resuscitator according to claim 1, wherein the inlet valve comprises a disc valve portion provided at the interior of the bag and an external annular portion which can be screwed onto the disc valve portion, and wherein the flow-through channel is provided in the disc valve portion.

13. Resuscitator according to claim 12, wherein the annular portion has a guide socket for at least partially receiving the container of the dosage aerosol which container is provided with a spraying valve.

14. Resuscitator according to claim 13, wherein the annular member is provided with a flow-through bore and a nipple for additional supply of oxygen.

15. Resuscitator according to claim 12, wherein the flow-through channel is arranged centrally in the middle of the inlet valve.

16. Method for providing a content of a dosage aerosol to a patient comprising the steps:

providing a resuscitator as defined in claim 1;

injecting into the bag a desired amount of content from the dosage aerosol through the flow through channel;

placing the resuscitator in relation to the patient; and, administering the content of the bag to the patient.

17. Method as described in claim 16, wherein the step of administrating is affected by compressing the bag of the resuscitator.

* * * * *

UNITED STATES PATENT AND TRADEMARK OFFICE
CERTIFICATE OF CORRECTION

PATENT NO. : 5,791,340
DATED : August 11, 1998
INVENTOR(S) : Petra Schleufe et al.

It is certified that error appears in the above-indentified patent and that said Letters Patent is hereby corrected as shown below:

On the Title Page after:
"[22] Filed: Sep. 16, 1996"
Insert:

--Related U.S. Application Data
--[63] Continuation of PCT DK/00122, Mar. 17, 1995, published as WO 95/24938, Sep. 21, 1995.--

Column 1, line 12, after "relates to" insert --device.--

Signed and Sealed this

Third Day of April, 2001

Attest:

NICHOLAS P. GODICI

*Attesting Officer*   *Acting Director of the United States Patent and Trademark Office*